United States Patent
Czaplewski et al.

(10) Patent No.: US 12,245,965 B2
(45) Date of Patent: Mar. 11, 2025

(54) OSTOMY APPLIANCE WITH FOLD-OVER FILTER

(71) Applicant: Hollister Incorporated, Libertyville, IL (US)

(72) Inventors: Gregory J. Czaplewski, Bloomingdale, IL (US); Rachel A. Hunt, Arlington Heights, IL (US); Mark W. Jockel, Vernon Hills, IL (US)

(73) Assignee: HOLLISTER INCORPORATED, Libertyville, IL (US)

( * ) Notice: Subject to any disclaimer, the term of this patent is extended or adjusted under 35 U.S.C. 154(b) by 428 days.

(21) Appl. No.: 17/911,967

(22) PCT Filed: Apr. 28, 2021

(86) PCT No.: PCT/US2021/029638
§ 371 (c)(1),
(2) Date: Sep. 15, 2022

(87) PCT Pub. No.: WO2021/225843
PCT Pub. Date: Nov. 11, 2021

(65) Prior Publication Data
US 2023/0172747 A1  Jun. 8, 2023

Related U.S. Application Data

(60) Provisional application No. 63/022,327, filed on May 8, 2020.

(51) Int. Cl.
*A61F 5/441*  (2006.01)
*A61F 5/44*   (2006.01)
*A61F 5/445*  (2006.01)

(52) U.S. Cl.
CPC ............ *A61F 5/441* (2013.01); *A61F 5/4404* (2013.01); *A61F 5/445* (2013.01)

(58) Field of Classification Search
CPC .......... A61F 5/441; A61F 5/4404; A61F 5/445
See application file for complete search history.

(56) References Cited

U.S. PATENT DOCUMENTS

| | | | | |
|---|---|---|---|---|
| 3,507,282 A | * | 4/1970 | Burding | A61F 5/445 604/333 |
| 3,655,118 A | * | 4/1972 | Rinecker | A44B 18/00 383/62 |

(Continued)

FOREIGN PATENT DOCUMENTS

| | | |
|---|---|---|
| AU | 2005282062 B2 | 7/2010 |
| EP | 0092299 B1 | 8/1987 |

OTHER PUBLICATIONS

International Search Report issued by ISA/EPO in connection with PCT/US2021/029638 on Aug. 12, 2021.

(Continued)

*Primary Examiner* — Guy K Townsend
(74) *Attorney, Agent, or Firm* — Klintworth & Rozenblat IP LLP

(57) ABSTRACT

An ostomy appliance (10) includes an outer wall (12) having first and second opposed sidewalls (14, 16) joined at an outer periphery (18), an inlet opening (22) and a filter (24). The outer wall (12) defines an interior volume (20) having a collection area. The ostomy appliance (10) further includes a fastener (32) on an external surface (30) of the outer wall (12). The fastener (32) is movable between a released state in which the ostomy appliance (10) is in an unfolded state, and a fastened state in which the ostomy appliance (10) is a folded state. The ostomy appliance (10), in the folded state, further includes a crease (40) positioned between the inlet opening (22) and the filter (24).

8 Claims, 5 Drawing Sheets

(56) References Cited

U.S. PATENT DOCUMENTS

| | | | | |
|---|---|---|---|---|
| 5,976,118 | A * | 11/1999 | Steer | A61F 5/445 604/332 |
| 6,336,918 | B1 * | 1/2002 | Olsen | A61F 5/4407 604/355 |
| 8,449,511 | B2 * | 5/2013 | Andersen | A61F 5/4404 604/326 |
| 11,071,640 | B2 * | 7/2021 | Fattman | A61F 5/4404 |
| 2004/0171999 | A1 * | 9/2004 | Andersen | A61F 5/445 604/332 |
| 2008/0097360 | A1 * | 4/2008 | Andersen | A61F 5/4404 604/332 |
| 2008/0300556 | A1 * | 12/2008 | Fenton | A61F 5/4404 604/339 |
| 2011/0028924 | A1 * | 2/2011 | Murray | A61F 5/4407 604/332 |
| 2012/0283678 | A1 * | 11/2012 | Nguyen-Demary | A61F 5/445 604/338 |
| 2015/0320585 | A1 * | 11/2015 | Fattman | A61F 5/4404 604/344 |
| 2016/0113810 | A1 * | 4/2016 | Hanuka | A61F 5/445 604/335 |
| 2021/0353448 | A1 * | 11/2021 | Fattman | A61F 5/443 |
| 2023/0081026 | A1 * | 3/2023 | Mahood | A61F 5/443 604/344 |
| 2023/0091863 | A1 * | 3/2023 | Brennan | A61F 5/4404 |

OTHER PUBLICATIONS

Written Opinion issued by ISA/EPO in connection with PCT/US2021/029638 on Aug. 12, 2021.

International Preliminary Report on Patentability issued by WIPO in connection with PCT/US2021/029638 dated Nov. 17, 2021.

* cited by examiner

OSTOMY APPLIANCE WITH FOLD-OVER FILTER

This is a National Stage Application of International Patent Application No. PCT/US2021/029638 filed Apr. 28, 2021, which claims the benefit of and priority to U.S. Provisional Application No. 63/022,327 filed May 8, 2020, the entirety of which are incorporated fully herein by reference.

BACKGROUND

The following description relates to an ostomy appliance, for example, a foldable ostomy appliance configured to prevent or limit accumulation of effluent at a filter.

A known ostomy appliance includes an ostomy bag which may be attached to a user and configured to collect effluent discharged from a stoma. The ostomy bag may include a filter through which gas may flow from an interior portion of the ostomy bag to the atmosphere. The filter may be an odor filter configured to filter odor from the gas accumulated in the ostomy bag.

However, in some instances, effluent discharged from the stoma and/or stored in the ostomy bag may accumulate on the filter and occlude or partially occlude the filter. An occluded filter may restrict gas flow from the interior of the ostomy bag to the atmosphere through the filter, which may result in an undesirable accumulation of pressure within the ostomy bag. This can lead to what is commonly referred to as "ballooning" of the ostomy bag.

Known ostomy bags have been formed with creases or folds to allow the ostomy bag to be folded to reduce size and unfolded to expand the size. Other known ostomy bags include pleats configured for directing the flow of gas within the ostomy bag. However, in such ostomy bags, effluent may still accumulate at or near the filter in a way which restricts air flow through the filter.

Accordingly, it is desirable to provide an ostomy appliance configured to prevent or limit accumulation of effluent at the filter.

SUMMARY

In one embodiment, an ostomy appliance may include an outer wall having first and second opposed sidewalls joined at an outer periphery, an inlet opening and a filter. The outer wall defines an interior volume comprising a collection area. The ostomy appliance may further include a fastener on an external surface of the outer wall. The fastener may be movable between a released state in which the ostomy appliance is in an unfolded state, and a fastened state in which the ostomy appliance is a folded state. In the folded state, the ostomy appliance may further include a crease positioned between the inlet opening and the filter.

In the unfolded state, the interior volume may be substantially continuous. In the folded state, the interior volume may be discontinuous. In the folded state, the crease may substantially restrict flow of effluent from the collection area to the filter.

The fastener may be a hook-and-loop fastener. The fastener may include a first fastener part and a second fastener part. The first fastener part and the second fastener part may be spaced from one another. The first fastener part may be one of a hook portion and a loop portion of a hook-and-loop fastener and the second fastener part may be the other of the hook portion and the loop portion of the hook-and-loop fastener.

In an embodiment, the fastener may be one or more of a hook-and-loop fastener, an adhesive, a button and a snap.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
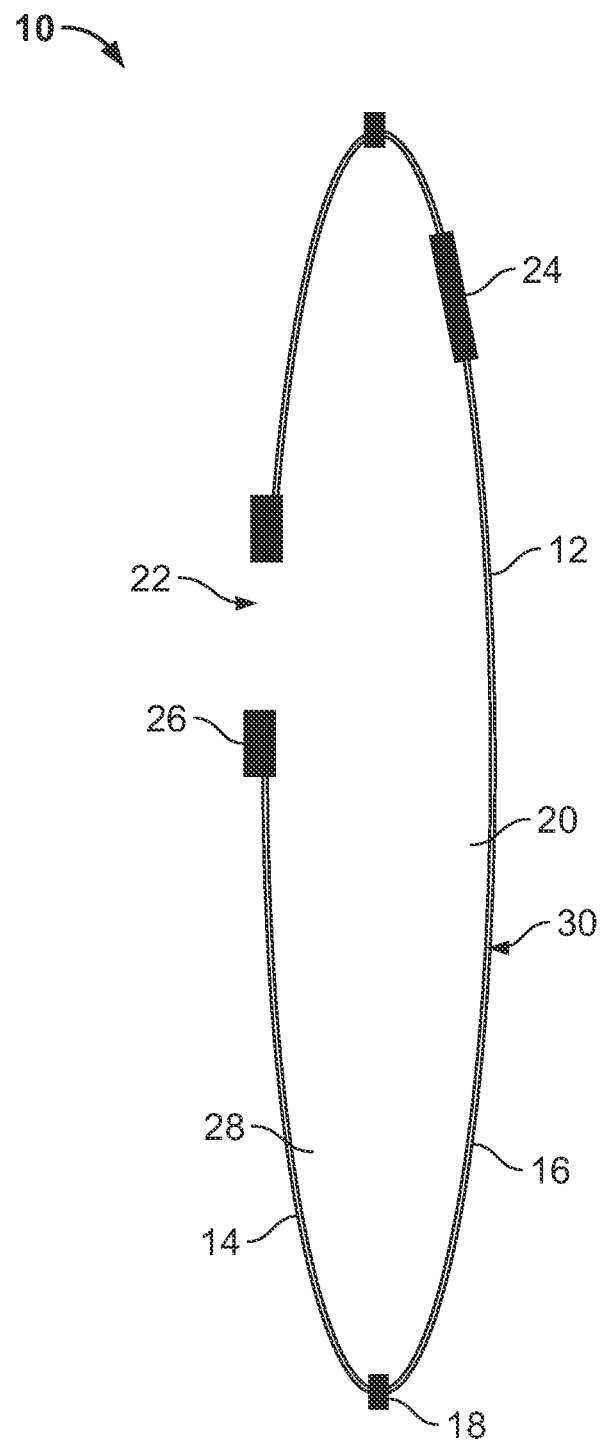
FIG. 1 is a diagram schematically illustrating a side cross-sectional view of an ostomy appliance, according to an embodiment.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

FIG. 1 is a diagram schematically illustrating a side cross-sectional view of an ostomy appliance 10, according to an embodiment. The ostomy appliance 10 may be an ostomy pouch. The ostomy appliance 10 may include an outer wall 12 having a first sidewall 14 and an opposed second sidewall 16 joined together at an outer periphery 18. The outer wall 12 may define an interior volume 20, for example, between the first sidewall 14 and the second sidewall 16. An inlet opening 22 may be included in one of the first sidewall 14 and the second sidewall 16 to allow for ingress effluent from a stoma to the interior volume 20.

The ostomy appliance 10 may further include a filter 24 connected to one of the first sidewall 14 and the second sidewall 16. The filter 24 may be disposed in fluid communication with the interior volume 20 and external atmosphere. Accordingly, gas from the interior volume 20 may be vented through the filter 22 to the external atmosphere. The filter 24 may be configured to deodorize the gas as the gas is vented through the filter 24. The filter 24 may be, for example, a charcoal filter.

In an embodiment, the first sidewall 14 may be a proximal side of the ostomy appliance 10. The inlet opening 22 may be formed in the first sidewall 14. The second sidewall 16 may be a distal side of the ostomy appliance 10. The filter 24 may be connected to the second sidewall 16.

The ostomy appliance 10 may also include a coupling flange 26 secured to the outer wall 12 adjacent to the inlet opening 22. In an embodiment, the coupling flange 26 may surround or substantially surround the inlet opening 22. The coupling flange 26 is configured to couple the ostomy appliance 10 to an ostomy faceplate (not shown) adhered to the user at an area around the stoma. In this manner, the ostomy appliance 10 may be secured to the user and may receive effluent from the stoma into the interior volume 20 through the inlet opening 22.

The interior volume 20 of the ostomy appliance 10 may include a collection area 28 configured to collect and store effluent received from the stoma. The collection area 28 may be a portion of the interior volume 20 generally below the inlet opening 22 and the filter 24 when the ostomy appliance 10 is secured to the user. For example, the inlet opening 22 and the filter 24 may be generally be disposed at an upper section of the ostomy appliance 10 and the collection area 28 may be formed in a lower section of the ostomy appliance 10. Further, in an embodiment, the filter 24 may be disposed above the inlet opening 22.

Figure 2:
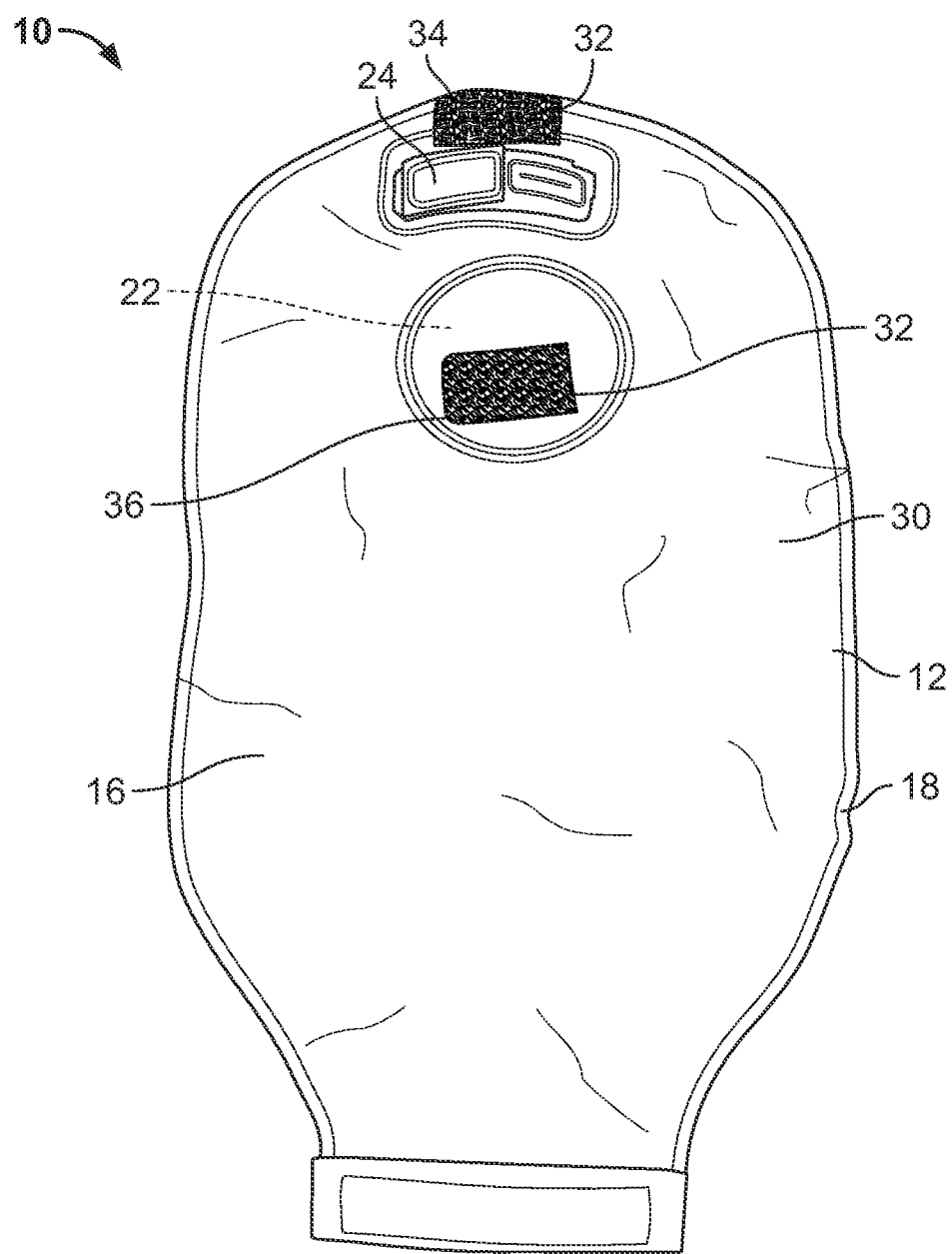
FIG. 2 is a plan view illustrating the ostomy appliance in an unfolded state, according to an embodiment.
Figure 3:
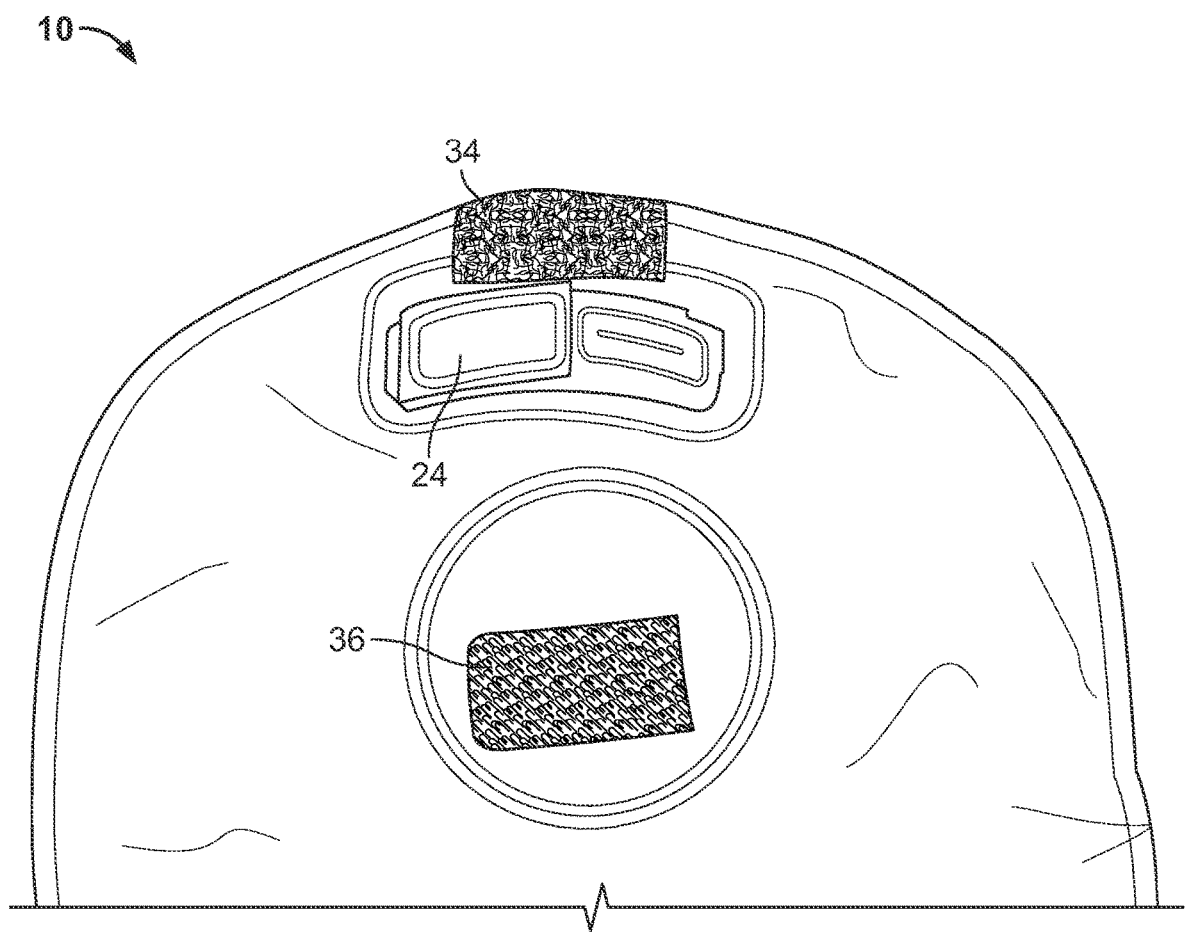
FIG. 3 is an enlarged plan view illustrating a portion of the ostomy appliance of FIG. 2.

FIG. 2 illustrates a plan view of the ostomy appliance 10 according to an embodiment. FIG. 3 is an enlarged plan view illustrating a portion of the ostomy appliance 10 of FIG. 2. The outer wall 12 includes an external surface 30. The ostomy appliance may include a fastener 32 on the external surface 30. The fastener 32 may include a first fastener part 34 and a second fastener part 36.

In an embodiment, the first fastener part 34 and the second fastener part 36 may be spaced apart along the height of the ostomy appliance 10. For example, the first fastener part 34 may be disposed adjacent to the filter 24 and the second fastener part 36 may be disposed below the filter 24 along the height of the ostomy appliance 10. In an embodiment, the second fastener part 36 may be disposed at height generally corresponding to a height at which the inlet opening 22 is disposed. In an embodiment, the first fastener part 34 and the second fastener part 36 may be disposed on the same sidewall as the filter 24. For example, the first fastener part 34 and the second fastener part 36 may be disposed on the second sidewall 16.

In an embodiment, the first fastener part 34 and the second fastener part 36 may be discontinuous and spaced apart from one another. Alternatively, or in addition, the first fastener part 34 and the second fastener part 36 may be formed continuously, for example, as a strip of fastener material. In an embodiment, a plurality of fasteners 32 may be provided. Accordingly, a corresponding plurality of first fastening parts 34 and second fastening parts 36 may be provided as well.

Referring still to FIGS. 2 and 3, the fastener 32 may be positioned in a released state in which the first fastener part 34 and the second fastener part 36 are disengaged and spaced from one another. The ostomy appliance 10 may be in an unfolded state when the fastener 32 is in the released state.

Figure 4:
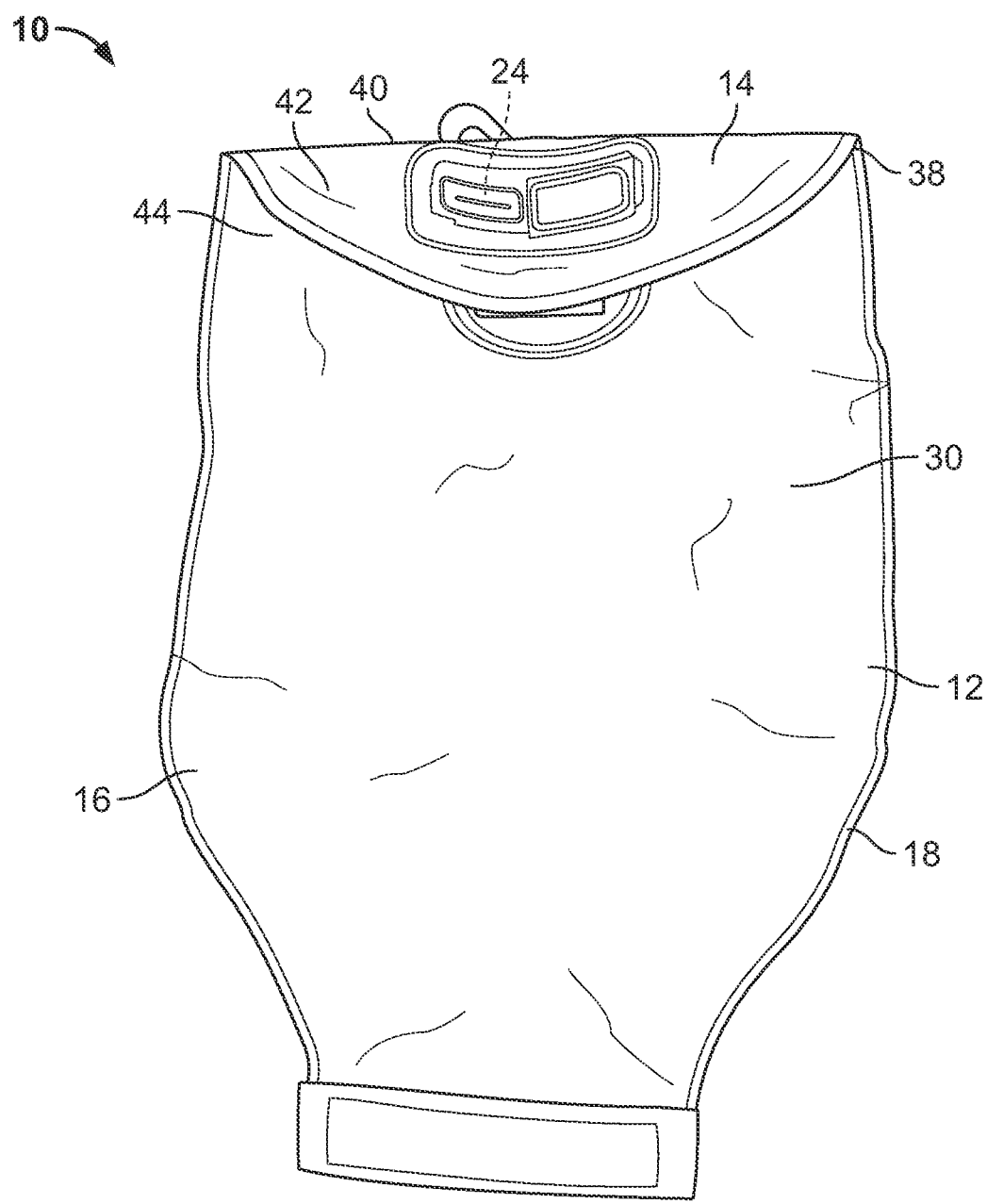
FIG. 4 is a plan view illustrating of the ostomy appliance in a folded state, according to an embodiment.
Figure 5:
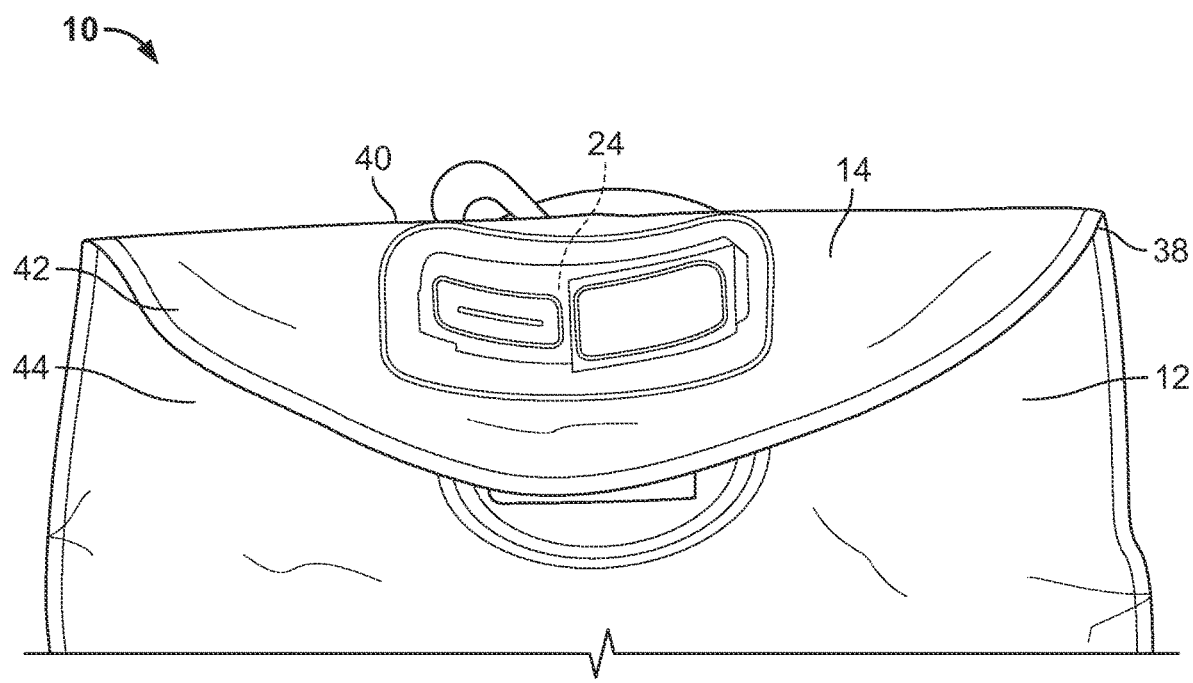
FIG. 5 is an enlarged plan view illustrating a portion of the ostomy appliance of FIG. 4.

FIG. 4 illustrates a plan view of the ostomy appliance 10 according to an embodiment. FIG. 5 is an enlarged plan view illustrating a portion of the ostomy appliance 10 of FIG. 4. The fastener 32 may also be positioned in a fastened state. In the fastened state, the first fastener part 34 and the second fastener part 36 are engaged with and secured to one another. The ostomy appliance 10 may be in a folded state when the fastener 32 is in the fastened state.

Accordingly, the fastener 32 may be moved between a released state and a fastened state to move the ostomy appliance 10 between an unfolded state and a folded state, respectively. The fastener 32 may be a releasable fastener. The fastener 32 may also be reusable such that it may be moved between the released state and fastened state numerous times.

In an embodiment, the fastener 32 may be a hook-and-loop fastener. In an embodiment, the first fastener part 34 may be one of a hook portion and a loop portion of the hook-and-loop fastener, and the second fastener part 36 may be the other of the hook portion and the loop portion. The first fastener part 34 and the second fastener part 36 may be secured to the outer wall 12 using a known, suitable fastener, such as an adhesive.

The fastener 32 is not limited to a hook-and-loop fastener, however. Other known, suitable fasteners capable of repeated fastening and release cycles (i.e., repeated movement between the fastened state and the released state) may be used as well. Such fasteners may include, for example, adhesives, buttons, snaps and the like. Combinations of different fasteners may be used as well.

In an embodiment, in the unfolded state, the interior volume 20 is substantially continuous. Accordingly, effluent may flow freely in the interior volume 20.

The ostomy appliance 10 may be folded over itself at a folding location 38, such as a folding line, between the first fastener part 34 and the second fastener part 36. The ostomy appliance 10 may be folded such that the first fastener part 34 and the second fastener part 36 are moved into the fastened state. In this manner, the ostomy appliance 10 may be moved to folded state. The ostomy appliance may be fastened to itself and held in the folded state by way of the fastener 32.

For example, the ostomy appliance 10 may be folded over itself to form a crease 40 at the folding location 38. The crease 40 may extend across a width of the ostomy appliance 10. The crease may be located between the inlet opening 22 and the filter 24 in a direction of gas flow from the collection area 28 to the filter 24.

In the folded state, the crease 40 may make the interior volume 20 discontinuous, such that flow of effluent is limited or restricted to predetermined portions of the interior volume 20. For example, the crease 40 may substantially prevent or limit effluent flow to the filter 24. Thus, effluent received through the inlet opening 22 and/or stored in the collection area 28 may be prevented from flowing to the filter 24 by the crease 40, with the crease 40 positioned between the inlet opening 22 and the filter 24. Accordingly, in the folded state, effluent may be substantially prevented from accumulating at the filter 24.

In an embodiment, in the folded state of the ostomy appliance 10, the crease 40 may still allow gas flow from the collection area 28 to the filter 24. Accordingly, the gas may be deodorized and vented from the interior volume 20 to the external atmosphere. Alternatively, or in addition, the fastener 32 may be moved to the released state and the ostomy appliance may be moved to the unfolded state to allow for gas flow, or additional gas flow relative to the folded state, from the collection area 28 to the filter 24. In this manner, a relatively higher volume flow of gas may be provided to the filter 24 to be deodorized and vented to the external atmosphere.

In an embodiment, the outer wall 12 may generally define an ostomy pouch body, and the ostomy pouch body may be moved between the folded and unfolded states as described in the embodiments above. In addition, with the folding location 38, such as a folding line or the like, disposed generally at an upper portion of the ostomy appliance 10, for example, between the inlet opening 22 and the filter 24, moving the ostomy appliance 10 between the folded and unfolded states in normal use does not affect capacity of the collection area 28, since the collection area 28, i.e., the portion of the interior volume 20 configured and intended to collect and store stomal effluent, is disposed below the inlet opening 22.

Further still, in the folded state of the ostomy appliance, the head space (e.g., a portion of the ostomy appliance 10 extending above the inlet opening 22) may be reduced. That is, by folding over the ostomy appliance onto itself at a folding location at or above the inlet opening 22, a footprint of the ostomy appliance may be reduced. Accordingly, discretion and comfort to the wearer may be improved.

For example, the folding location may be line extending across the width of the ostomy appliance 10 and may be positioned, for example, at or slightly above an upper portion of the coupling flange 26. In one embodiment, the folding location may be a line extending tangential to an upper portion of the coupling flange 26. In another embodiment, the folding location may be spaced from the coupling flange 26.

Referring again to FIGS. 4 and 5, in the folded state, a folded portion 42 of the ostomy appliance 10, i.e., a portion above the folding location 38 may folded over onto a base portion 44 of the ostomy appliance 10, i.e., a portion below the folding location 38. The crease 40 may be formed at the folding location. The folded portion 42 may be releasably secured to the base portion 44 by the fastener 32 in the fastened state. In this manner, the footprint of the ostomy appliance 10 may be reduced.

In addition, because the crease 40 may restrict gas flow toward the filter 24, a potential ballooning volume may be reduced as well, which may further improve discretion and comfort for the wearer. In the event of ballooning, the folded portion 42 may remain secured to the base portion 44 by the fastener 32 to resist unfolding of the ostomy appliance 10.

It is understood that the relative directions described above, e.g., "upward," "downward," "upper," "lower," "above," "below," are used for illustrative purposes only and may change depending on an orientation of the ostomy pouch and/or the patient. Accordingly, this terminology is non-limiting in nature. In addition, it is understood that one or more various features of an embodiment above may be used in, combined with, or replace other features of a different embodiment described herein.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy appliance comprising:
an outer wall having first and second opposed sidewalls joined at an outer periphery, an inlet opening and a filter, wherein the outer wall defines an interior volume comprising a collection area, and
a fastener on an external surface of the outer wall, the fastener movable between a released state in which the ostomy appliance is in an unfolded state, and a fastened state in which the ostomy appliance is a folded state, wherein the ostomy appliance, in the folded state, further includes a crease positioned between the inlet opening and the filter.

2. The ostomy appliance of claim 1, wherein in the unfolded state, the interior volume is substantially continuous, and in the folded state, the interior volume is discontinuous.

3. The ostomy appliance of claim 1, wherein in the folded state, the crease substantially restricts flow of effluent from the collection area to the filter.

4. The ostomy appliance of claim 1, wherein the fastener is a hook-and-loop fastener.

5. The ostomy appliance of claim 1, wherein the fastener includes a first fastener part and a second fastener part.

6. The ostomy appliance of claim 5, wherein the first fastener part and the second fastener part are spaced from one another.

7. The ostomy appliance of claim 1, wherein the first fastener part is one of a hook portion and a loop portion of a hook-and-loop fastener and the second fastener part is the other of the hook portion and the loop portion of the hook-and-loop fastener.

8. The ostomy appliance of claim 1, wherein the fastener is one or more of a hook-and-loop fastener, an adhesive, a button and a snap.

* * * * *